United States Patent [19]
Millet

[11] 4,015,709
[45] Apr. 5, 1977

[54] SYRINGE PACKAGE

[75] Inventor: Marcus Jacob Millet, New York, N.Y.

[73] Assignee: Johnson & Johnson, New Brunswick, N.J.

[22] Filed: Oct. 28, 1975

[21] Appl. No.: 626,436

[52] U.S. Cl. .............................. 206/366; 206/526; 206/521; 206/523
[51] Int. Cl.² .................. B65D 85/62; B65D 81/04
[58] Field of Search .......... 206/370, 461, 523, 521, 206/365, 366, 72, 73, 45.14, 44 R, 44.11, 332, 328, 526; 229/48 T, 48 SB; 53/37

[56] References Cited
UNITED STATES PATENTS

| | | | |
|---|---|---|---|
| 3,010,570 | 11/1961 | Sandstrom | 215/231 |
| 3,013,656 | 12/1961 | Murphy, Jr. | 206/72 |
| 3,049,224 | 8/1962 | Fredette et al. | 229/48 SB |
| 3,275,329 | 9/1966 | Lieberman et al. | 206/72 |
| 3,429,096 | 2/1969 | Griese, Jr. | 53/37 |
| 3,670,872 | 6/1972 | Rock et al. | 206/44 R |
| 3,756,399 | 9/1973 | Cosier et al. | 206/328 |
| 3,850,296 | 11/1974 | Hirata et al. | 206/73 |

*Primary Examiner* — William T. Dixson, Jr.

[57] ABSTRACT

A container in the form of an elongated tray for packaging a plurality of syringes and subsequently forming a rack when inverted for holding the syringes prior to and after use. The tray may have an open top, enclosed side walls and an enclosed bottom wall having an external surface with at least one row of notches for holding and accurately positioning the syringes. A removable label or cover may be heat-sealed or otherwise secured over the open top of the tray. In one embodiment of the invention, a heat-sealable dunnage material may be positioned in the tray between the cover and the syringes and both the dunnage material and the tray may be heat-sealed to the cover to thereby facilitate removal of the dunnage material. The method of utilizing the heat-sealable dunnage material is also disclosed.

11 Claims, 8 Drawing Figures

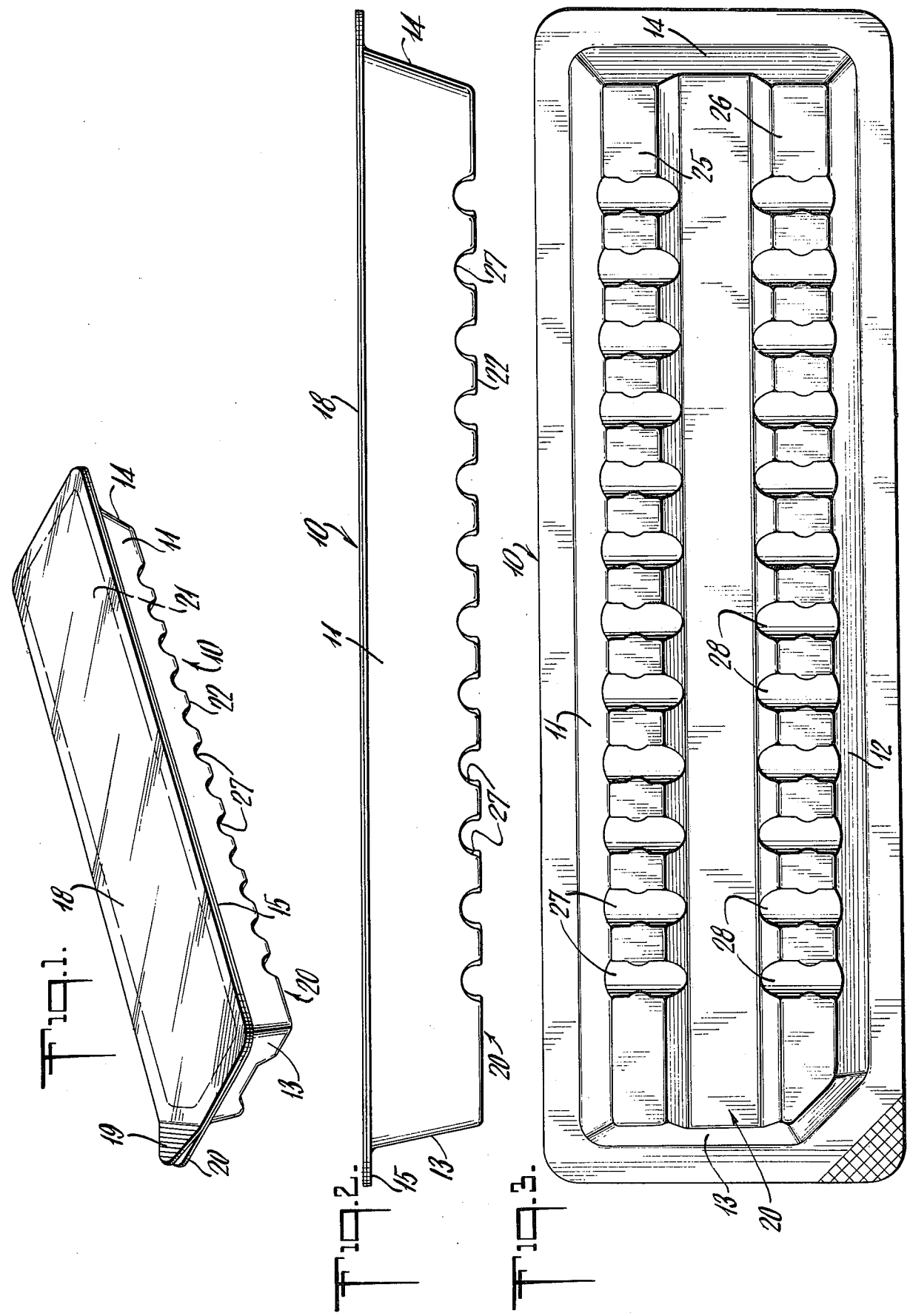

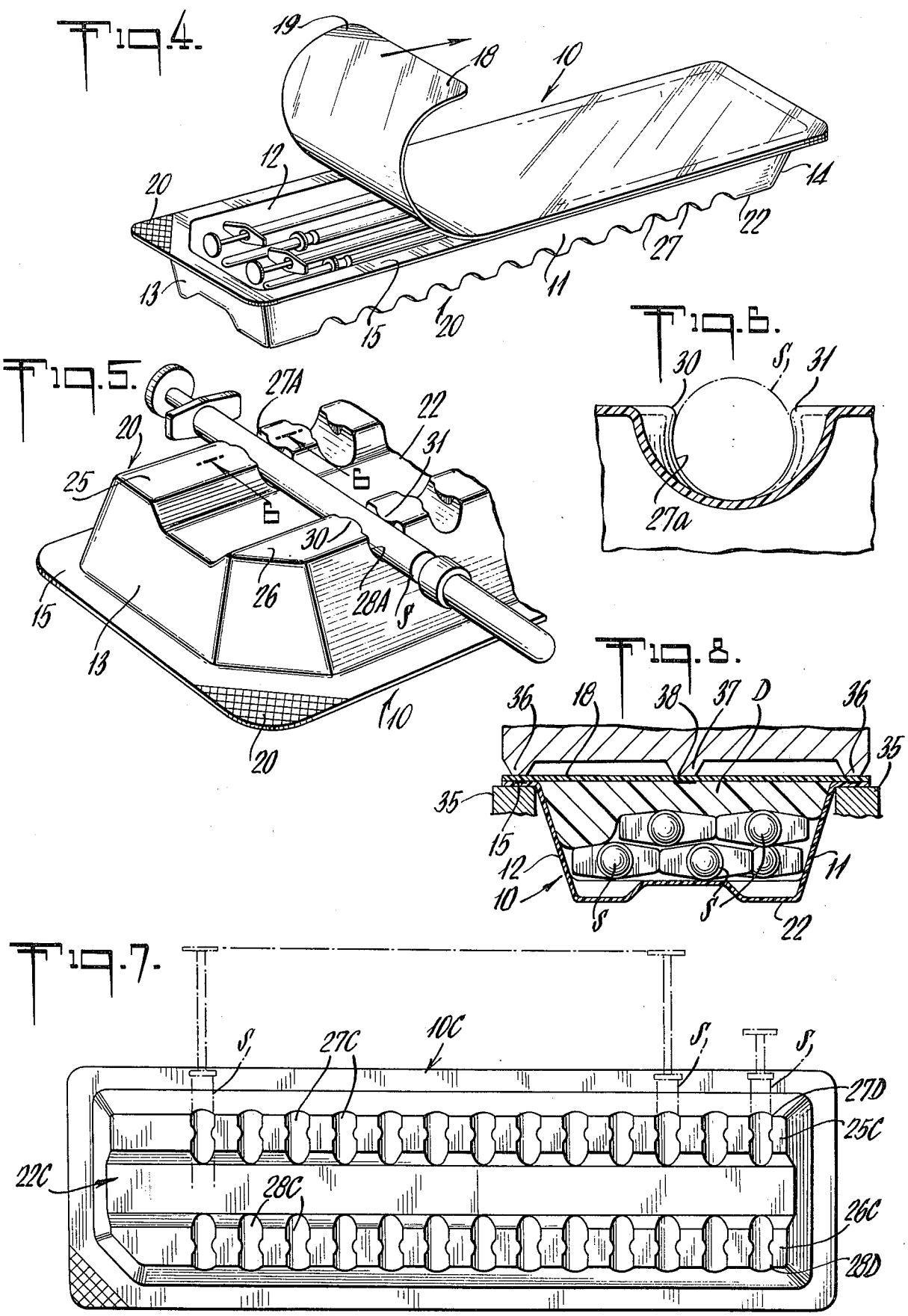

SYRINGE PACKAGE

BACKGROUND OF THE INVENTION

This invention relates to a unique package for syringes and, more particularly, the invention relates to a package having a unique external surface on the bottom wall thereof which can be used to hold the syringes after they have been removed from the package and prior to and after use. The invention further relates to a unique system for handling the dunnage material normally used in packaging and to a method for applying such dunnage material to the package.

Although the present invention may be utilized with all types of syringes, it has particular applicability for use with allergist's syringes. In the normal situation, the allergist prefers to purchase a group of syringes in a single sterile package. All of the syringes in the package are identical before they are filled. However, a technician or assistant normally fills each syringe with a different fluid before presenting the entire group to the allergist for use. Thus, it is essential to maintain the syringes in an ordered array between the time of filling and the time of use. Heretofore, there have been two approaches used in the packaging of syringes for this procedure. In one approach, the syringes were simply placed in random order in a sterile container, with no provision for the holding of the syringes in an ordered array between filling and use. In the other approach, the syringes were pre-packaged in a tray with notches which held the syringes in an ordered array before filling. Although this approach provided for the maintenance of order after filling, it also required that the technician extract each syringe from its position in order to fill it. Also, to provide an ordered array with one syringe in each notch, this type of tray required a projected area at least equal to the product of the length of each syringe and the center-to-center distance between adjacent syringes, multiplied by the number of syringes in the package. As the cost of formed thermoplastic packaging material is substantially proportional to the projected area of the package, packages designed by the second approach were quite expensive to produce.

SUMMARY OF THE INVENTION

The present invention is intended to overcome the difficulties encountered in prior multiple syringe packages. This is accomplished by providing a container in the form of an elongated tray for packaging a plurality of syringes in bulk and for subsequently forming a rack when inverted for holding the syringes between filling and use and after use. The container is preferably provided with four side walls and a bottom wall which has an external surface with at least one row of syringe supporting members.

In the preferred embodiment, the syringe supporting members are in the form of a pair of rows of notches which support the individual syringes transversely of the package. A removable label or cover is heat-sealed or otherwise secured over the open top of the tray and in one embodiment of the invention, a heat-sealable dunnage material may be positioned in the tray between the cover and the syringes and also heat-sealed to the cover so that it may be removed from the tray simultaneously with the removal of the label or cover.

The unique structure of the external surface of the bottom of the tray greatly facilitates the handling of the syringes by the physician after filling. The syringes are preferably firmly held within the notches and the notches are designed so that handling of the syringes is greatly facilitated.

In one embodiment of the invention, an additional pair of notches is provided so that a space may be left between the last used syringe and the syringe that is next to be used so that inadvertent use of the syringes is eliminated.

BRIEF DESCRIPTION OF THE DRAWINGS

The invention will be particularly described with reference to the following detailed description of the preferred embodiment of the invention when considered together with the attached drawings in which:

FIG. 1 is a perspective view illustrating the unique syringe package of the present invention;

FIG. 2 is a side view of the syringe package illustrated in FIG. 1;

FIG. 3 is a bottom plan view of the syringe package illustrated in FIG. 1;

FIG. 4 is a perspective view similar to FIG. 1 but showing the top label or cover peeled partially away from the remainder of the package.

FIG. 5 is a fragmentary perspective view of the bottom portion of the package illustrating a syringe positioned thereon;

FIG. 6 is a cross sectional view taken along line 6—6 in FIG. 5;

FIG. 7 is a bottom plan view of another embodiment of the syringe package illustrated in FIG. 3; and FIG. 8 is a cross sectional view illustrating the preferred method for sealing the label onto the syringe package.

DESCRIPTION OF THE PREFERRED EMBODIMENTS

Referring to the drawings, the unique syringe package of the present invention is illustrated generally by numeral 10. Package 10 is a generally elongated rectangular structure having opposed side walls 11 and 12 and opposed end walls 13 and 14. The top of package 10 is preferably open and has an outwardly extending flange 15 completely around the periphery thereof to which a label or cover 18 may be heat-sealed, or otherwise secured.

As illustrated best in FIG. 4, cover 18 is heat-sealed completely around its outer peripheral edge to flange 15 and a small corner 19 is unsecured to the flange at corner 20 so that the cover may be easily grasped for removal from the package. Package 10 may be formed from any convenient material; however, it is preferably a thermal formed blister formed from a suitable plastic material. Likewise, the material from which cover 18 is constructed is not critical so long as it may be heat-sealed, or otherwise secured, to flange 15. Of course, it is desirable that all materials from which the package is made be sterilizable.

Package 10 has a bottom wall 20 which has an internal surface 21 and an external surface 22. Referring to FIG. 3, external surface 22 of bottom wall 20 is illustrated in detail. Formed integral with external surface 22 is a pair of raised ribs 25 and 26 which extend longitudinally of the elongated package 10. A plurality of notches 27 are formed along the length of rib 25 and a plurality of notches 28 are formed along the length of rib 26. Notches 27 and 28 are in transversely aligned relationship to form two rows of syringe receiving and holding members. It will be seen from FIG. 5, that a pair of aligned notches 27A and 28A are positioned to receive one of the syringes S that is initially packaged within package 10. In a similar manner, the remaining syringes within package 10 may be appropriately positioned in the other matching pairs of notches 27 and 28 which are located along the length of ribs 25 and 26. In order to securely hold the syringes in place, notches 27 and 28 are preferably dimensioned to approximate the circumference of the syringes. A pair of inwardly directed projections 30 and 31 is formed at the upper portion of each notch to provide a "snap" fit for the syringes. This is best illustrated in FIGS. 5 and 6, wherein syringe S is shown securely positioned within notches 27A and 28A with projections 30 and 31 firmly holding the syringe in place.

The manner of utilizing the unique package of the subject invention will be easily appreciated from the foregoing description. A predetermined number of syringes is packaged within package 10 by the syringe manufacturer and label or cover 18 is then preferably heat-sealed around the periphery of the top of the package to flange 15. The number of syringes contained within package 10 is normally determined by the normal practice of the allergist and the only requirement is that there be at least an equal number of matching notches 27 and 28 for each syringe contained in the package.

When the syringe package has been received and is ready for use by the allergist, the allergist or an assistant may remove cover 18 from the package by pulling tab 19 upwardly while at the same time holding corner 20. The syringes may then be removed from the package by simply inverting it and preferably placed on a sterile field for subsequent filling. After each syringe has been filled, it is appropriately positioned within a pair of notches 27 and 28 on the external surface of bottom wall 20 after the package has been inverted with flange 15 facing a table, or other supporting, surface. When all of the syringes have been filled and appropriately positioned within their respective notches, the entire assembly is now ready for use.

It will be noted from FIG. 5, that the unique structure of external surface 22 and the dimensioning of ribs 25 and 26 permits the syringes to be placed substantially transversely to the longitudinal axis of package 10 so that the syringes will extend beyond the ribs in order to facilitate handling of the syringes. Also, in the preferred embodiment illustrated in FIG. 5, a central depression extends the entire length of the package between ribs 25 and 26 to further facilitate handling of the syringes. After each syringe has been utilized by the allergist, it may then be replaced into its initial position within notches 27 and 28 and in this manner the allergist is able to easily and conveniently maintain an accurate count of the number of syringes that he utilizes.

In one embodiment of this invention, as best illustrated in FIG. 7, an additional pair of notches 27 and 28 may be added to the package in order to provide an additional means for locating and keeping track of the syringes. In the embodiment illustrated in FIG. 7, package 10C has an external surface 22C on the bottom wall thereof which has a pair of ribs 25C and 26C formed therein. Ribs 25C and 26C are substantially parallel and run the complete length of package 10C. Opposed notches 27C and 28C are formed in ribs 25C and 26C, respectively, for holding syringes in a manner described above. The only difference between the embodiment of FIG. 7 and the embodiment illustrated in the other Figures, is the provision in the FIG. 7 embodiment of an additional pair of notches 27D and 28D. The use of the word "additional" is intended to mean that there is one more set of opposed notches than the number of syringes initially packaged within package 10C. The reason for providing notches 27D and 28D is to provide an even further means for accurately locating and keeping track of the syringes while they are being utilized by the allergist.

For example, when the syringes packaged in package 10C are completely filled and ready for use they would be positioned within the first 12 sets of notches 27C and 28C provided on the left portion of the package as illustrated in FIG. 7. Notches 27D and 28D would be initially empty. Following the use of the first syringe in the set of notches 27C and 28C immediately adjacent notches 27D and 28D, the syringe would then be placed into notches 27D and 28D thus leaving a space between that syringe and the next adjacent syringe. This procedure would be followed until all of the syringes have been utilized by the allergist. Thus, the allergist would always know that the next syringe to be used would be the syringe immediately to the left of the empty set of notches as viewed in FIG. 7.

As a further aspect of this invention, reference is made to FIG. 8 in which the use of a dunnage material D in combination with the unique package of this invention is illustrated.

The use of a dunnage material for packaging syringes, as well as many other articles, is very common. Dunnage material normally is placed into a package in a location between the packaged articles and the cover of the package in order to reduce movement of the articles and any damage to the articles that may result from this movement.

As illustrated in FIG. 8, package 10 is shown with a plurality of syringes S resting on the internal surface of the bottom wall thereof. Above syringes S is positioned a dunnage material D which is a relatively soft, pliable material that is designed to conform to the general contour of the uppermost layer of the syringes. As stated above, dunnage material of this general type has been utilized extensively in the past but, heretofore, the removal of such dunnage material from a package has always required a second manipulative step following the initial step of removing the cover or top of the package.

This second manipulative step is eliminated in the present invention by providing a dunnage material that may be heat-sealed, or otherwise secured, to the under surface of the package cover. In the preferred embodiment, dunnage material D is a thermoplastic foam material which is positioned within package 10 as illustrated in FIG. 8 and simultaneously heat-sealed to cover 18 when the cover is heat-sealed to flange 15 extending around the open periphery of package 10. As illustrated in FIG. 8, cover 18 is secured to flange 15 by a heat-sealing die having a lower peripheral member 35 which extends around the under surface of flange 15 and an upper peripheral member 36 which extends around the periphery of cover 18. A central heat sealing member 37 is provided on the upper die member to heat-seal cover 18 to dunnage material D at location 38 simultaneously with the other heat-sealing operation.

It will be apparent from the foregoing description that dunnage material D may be easily removed from package 10 during the removal of cover 18 and, thus, eliminate the further step of removing the dunnage as was heretofore required. This advantage is accomplished without the requirement of additional manufacturing steps and additional cost.

It will be apparent from the foregoing description, that the unique package of the subject invention provides numerous advantages over previously existing packages. The unique external surface of the bottom wall of the package provides a convenient means for presenting the filled syringes to the allergist and firmly holding them in aligned position both prior to and subsequent to their use. In addition, the invention provides a unique package in which the dunnage material may be removed therefrom simultaneously with the removal of the package cover.

What is claimed is:

1. A container for a plurality of syringes, comprising: an elongated tray having an open top, enclosed side walls and an enclosed bottom wall, said bottom wall having an internal surface and an external surface; and means on the external surface of said bottom wall for holding said plurality of syringes after said syringes have been removed from said container and said container has been placed in an inverted position with said top facing downwardly.

2. The container of claim 1, wherein said holding means is a plurality of substantially transversely aligned notches extending in a row along the length of said bottom wall.

3. The container of claim 2, wherein a second row of notches is positioned parallel to said other row and spaced therefrom so that a single syringe may be held by two of said spaced notches.

4. The container of claim 2, wherein said notches are shaped to conform generally to the contour of a syringe barrel and having inwardly directed projections on opposed surfaces to firmly but releasably hold said syringes within said notches.

5. A syringe package, comprising: an elongated tray having an open top, enclosed side walls and an enclosed bottom wall, said bottom wall having an internal surface and an external surface; a plurality of syringes disposed in said tray on said internal surface; a removable cover secured over said open top of said tray; and means on said external surface for holding said syringes in spaced relation after said cover has been removed from said top, said syringes have been removed from said package and said package has been placed in an inverted position with said top facing downwardly.

6. The package of claim 5, wherein said holding means comprises at least one row of spaced substantially transversely aligned syringe holding members.

7. The package of claim 6, wherein said members are concave notches formed in said external surface.

8. The package of claim 7, wherein said holding means comprises spaced parallel rows of said notches.

9. The package of claim 5, wherein said removable cover is heat-sealed around the periphery of said open top of said tray.

10. The package of claim 9, further comprising a heat-sealable dunnage material positioned between said syringes and said removable cover and heat-sealed to said removable cover.

11. The package of claim 10, wherein said dunnage material is a thermoplastic foam.

* * * * *